United States Patent
Hebestreit et al.

(10) Patent No.: US 11,041,846 B2
(45) Date of Patent: Jun. 22, 2021

(54) TEST ELEMENT ANALYSIS SYSTEM FOR THE ANALYTICAL EXAMINATION OF A SAMPLE

(71) Applicant: Roche Diagnostics Operations, Inc., Indianapolis, IN (US)

(72) Inventors: Kai Hebestreit, Heidelberg (DE); Sylvia Saecker, Mannheim (DE); Klaus Thome, St. Leon-Rot (DE); Andreas Weller, Heidelberg (DE); Robert Knapstein, Heidelberg (DE); Werner Heidt, Darmstadt (DE); Stefan Lieder, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 252 days.

(21) Appl. No.: 16/106,889

(22) Filed: Aug. 21, 2018

(65) Prior Publication Data
US 2018/0356391 A1 Dec. 13, 2018

Related U.S. Application Data

(63) Continuation of application No. PCT/EP2017/055309, filed on Mar. 7, 2017.

(30) Foreign Application Priority Data

Mar. 8, 2016 (EP) .................................. EP16159147

(51) Int. Cl.
*G01N 25/00* (2006.01)
*G01K 1/00* (2006.01)
(Continued)

(52) U.S. Cl.
CPC ... *G01N 33/48785* (2013.01); *A61B 5/14532* (2013.01); *G01N 25/00* (2013.01);
(Continued)

(58) Field of Classification Search
USPC .................................. 374/43, 208, 141, 163
See application file for complete search history.

(56) References Cited

U.S. PATENT DOCUMENTS

| 3,704,099 A | 11/1972 | Sanz |
| 8,491,185 B2 | 7/2013 | Steinboeck et al. |

(Continued)

FOREIGN PATENT DOCUMENTS

| EP | 1543935 A2 | 6/2005 |
| EP | 2199792 A1 | 6/2010 |

(Continued)

OTHER PUBLICATIONS

International Search Report dated May 8, 2017, in Application No. PCT/EP2017/055309, 3 pp.
(Continued)

*Primary Examiner* — Mirellys Jagan
(74) *Attorney, Agent, or Firm* — Roche Diagnostics Operations, Inc.

(57) ABSTRACT

A test element analysis system for the analytical examination of a sample is disclosed. The test element analysis system comprises: at least one evaluation device with at least one test element holder for positioning a test element containing the sample and at least one measuring device for measuring a change in a measuring zone of the test element, the change being characteristic for the analyte; at least one electrical heating element configured for electrically heating the test element; at least one electrical power supply for supplying electrical energy to the electrical heating element; at least one temperature sensor connected to the test element holder for detecting a temperature of the test element holder; at least one gap detection device configured for monitoring the electrical energy $E_{spez}$ supplied by the electrical power supply to the electrical heating element for reaching a (Continued)

predetermined target temperature measured by the temperature sensor.

16 Claims, 4 Drawing Sheets

(51) Int. Cl.
  *G01K 7/00* (2006.01)
  *G01N 33/487* (2006.01)
  *G01N 27/327* (2006.01)
  *A61B 5/145* (2006.01)
  *G01N 33/49* (2006.01)

(52) U.S. Cl.
  CPC ..... *G01N 27/3273* (2013.01); *G01N 33/4905* (2013.01); *A61B 5/145* (2013.01)

(56) References Cited

U.S. PATENT DOCUMENTS

| | | |
|---|---|---|
| 2003/0220583 A1 | 11/2003 | Kurkowski et al. |
| 2005/0135968 A1 | 6/2005 | Augstein |
| 2006/0035298 A1 | 2/2006 | Hill et al. |
| 2006/0140822 A1* | 6/2006 | Krysl ................. G01N 33/4925 422/108 |
| 2007/0230535 A1* | 10/2007 | Atwood .................... B01L 7/52 374/1 |
| 2009/0092169 A1* | 4/2009 | Hallen ................... G01K 17/00 374/33 |
| 2010/0158070 A1 | 6/2010 | Steinboeck et al. |
| 2010/0309947 A1* | 12/2010 | Parasnis ............... G01K 15/005 374/1 |

FOREIGN PATENT DOCUMENTS

| | | |
|---|---|---|
| WO | 2012/040050 A1 | 3/2012 |
| WO | 2014/045057 A2 | 3/2014 |
| WO | 2014/198428 A1 | 12/2014 |

OTHER PUBLICATIONS

Hoenes, Joachim et al., The Technology Behind Glucose Meters: Test Strips, Diabetes Technology & Therapeutics, 2008, pp. S-10-S-26, vol. 10, Supplement 1.

* cited by examiner

TEST ELEMENT ANALYSIS SYSTEM FOR THE ANALYTICAL EXAMINATION OF A SAMPLE

CROSS-REFERENCE TO RELATED APPLICATIONS

This application is a continuation of International Patent Application No. PCT/EP2017/055309, filed 7 Mar. 2017, which claims the benefit of European Patent Application No. 16159147.4, filed 8 Mar. 2016, the disclosures of which are hereby incorporated herein by reference in their entirety.

TECHNICAL FIELD

The present disclosure relates to a test element analysis system for the analytical examination of a sample and a method for determining whether a test element located inside a test element holder of a test element analysis system for the analytical examination of a sample has sufficient thermal contact with an electrical heating element configured for electrically heating the test element. The devices and methods according to the present disclosure mainly may be used in the field of qualitatively or quantitatively detecting at least one analyte in a sample, such as a sample of a body fluid, and/or for determining at least one parameter of the sample. Other fields of application are feasible.

BACKGROUND

In the field of medical technology and diagnostics, a large number of devices and methods for determining the presence and/or the concentration of one or more analytes in samples, specifically fluid samples, such as body fluids, and/or for determining at least one parameter of a sample are known. Without restricting the scope of the present disclosure, in the following, mainly reference is made to the determination of coagulation parameters in blood samples or to blood glucose concentrations. It shall be noted, however, that other types of samples or other types of analytes or parameters may be used in a similar way.

For performing fast and simple measurements, several types of test elements are known, which mainly are based on the use of one or more test chemicals, i.e., on the use of one or more chemical substances, one or more chemical compounds or one or more chemical mixtures, adapted for performing a detection reaction for detecting the analyte or determining the parameter. The test chemical often is also referred to as a test substance, a test reagent, a test chemistry or as a detector substance. For details of potential test chemicals and test elements comprising such test chemicals, which may also be used within the present disclosure, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present disclosure.

By using one or more test chemicals, a detection reaction may be initiated, the course of which depends on the presence and/or the concentration of the at least one analyte or on the parameter to be determined. The detection reaction typically may be analyte-specific. Typically, as may also be the case in the present disclosure, the test chemical is adapted to perform at least one detection reaction when the analyte is present in the body fluid, wherein the extent and/or the degree of the detection reaction typically depends on the concentration of the analyte. Generally, the test chemical may be adapted to perform a detection reaction in the presence of the analyte, wherein at least one detectable property of at least one of the body fluid and the test chemical is changed due to the detection reaction. The at least one detectable property generally may be selected from a physical property and a chemical property. In the following, without restricting potential other embodiments, reference will mainly be made to detection reactions in which one or more physical properties are changed due to the detection reaction, such as one or more of at least one electrical property and at least one optical property. Further, without restricting alternative solutions, reference will be made to detection reactions in which at least one chemical property which is electrically detectable is changed, i.e., to electrochemical test elements. Other test elements, such as optical test elements, however, are usable, too.

As generally known in the art of chemical analytics, the detection reaction and, thus, the measurement result may strongly depend on the temperature of the test element, specifically on the temperature in a reaction zone or measurement zone of the test element, and/or of the sample. A precise temperature control of the test element and/or a precise monitoring of the temperature of the test element is therefore desirable, in order to increase the accuracy of the measurement. Therefore, several known devices generally provide a heating device for heating the test element and further are equipped to monitor the temperature of the test element, in order to safeguard a sufficient thermal coupling between the heating device and the test element. Specifically, mechanical displacements during handling of the test element analysis system, such as mechanical shocks caused by dropping the analysis system with the test element disposed therein, may deteriorate a thermal contact between the test element and the heating element. Further, during handling of the test element analysis system without the test element disposed therein, mechanical displacements of the test element holder and/or of the electrical heating element may occur such as by dropping the analysis system. Consequently, the thermal contact between the test element and contacts of the test element analysis system may be affected.

Despite of the advantages implied by these devices and methods, known devices and methods for temperature control, however, imply several technical challenges. Thus, known devices and methods generally rely on the use of temperature sensors or temperature-sensitive elements located on the test element itself. In these setups, additional temperature sensors have to be implemented into the test elements, which generally renders the test elements and the evaluation device contacting the test element more complex and, thus, more costly. Alternatively, sensor elements which are already present on the test element may additionally be used for temperature control, as in U.S. Pat. No. 8,491,185 B2 or in EP 2 199 792 B1. This alternative, however, requires additional electronics and evaluation devices for applying an additional measurement signal to the test element and for evaluating the response of the test element to this measurement signal, in order to evaluate the thermal coupling between the test element and thermostatted element of the evaluation device.

BRIEF SUMMARY

It is against the above background that the embodiments of the present disclosure provide certain unobvious advantages and advancements over the prior art. In particular, the inventors have recognized a need for improvements in a test element analysis system for the analytical examination of a sample.

Although the embodiments of the present disclosure are not limited to specific advantages or functionality, it is noted that a test element analysis system for the analytical examination of a sample is disclosed that enables a simple and cost-efficient monitoring of a thermal coupling between a heating element and a test element, typically without additional measurement setups relying on measurements inside or on the test element.

In accordance with one embodiment of the present disclosure, a test element analysis system for the analytical examination of a sample, in particular of a body fluid, is provided comprising: at least one evaluation device with at least one test element holder for positioning a test element containing the sample and at least one measuring device for measuring a change in a measuring zone of the test element, the change being characteristic for the analyte; at least one electrical heating element configured for electrically heating the test element; at least one electrical power supply for supplying electrical energy to the electrical heating element; at least one temperature sensor connected to the test element holder for detecting a temperature of the test element holder; at least one gap detection device configured for monitoring the electrical energy $E_{spez}$ supplied by the electrical power supply to the electrical heating element for reaching a predetermined target temperature measured by the temperature sensor, wherein the gap detection device is configured for evaluating the electrical energy $E_{spez}$ supplied by the electrical power supply to the electrical heating element for reaching the predetermined target temperature and to derive at least one item of information on a thermal contact between the electrical heating element and the test element based on the evaluation of the electrical energy $E_{spez}$.

In accordance with another embodiment of the present disclosure, a method for determining whether a test element located inside a test element holder of a test element analysis system for the analytical examination of a sample has sufficient thermal contact with an electrical heating element configured for electrically heating the test element is provided, the method comprising: a) inserting the test element into the test element holder; b) heating the test element to a predetermined target temperature by using the electrical heating element; c) monitoring the electrical energy $E_{spez}$ supplied by an electrical power supply to the electrical heating element for reaching the predetermined target temperature of the electrical heating element; d) evaluating the electrical energy $E_{spez}$ supplied by the electrical power supply to the electrical heating element for reaching the predetermined target temperature of the electrical heating element and deriving thereof at least one item of information on a thermal contact between the electrical heating element and the test element.

These and other features and advantages of the embodiments of the present disclosure will be more fully understood from the following description in combination with the drawings and the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
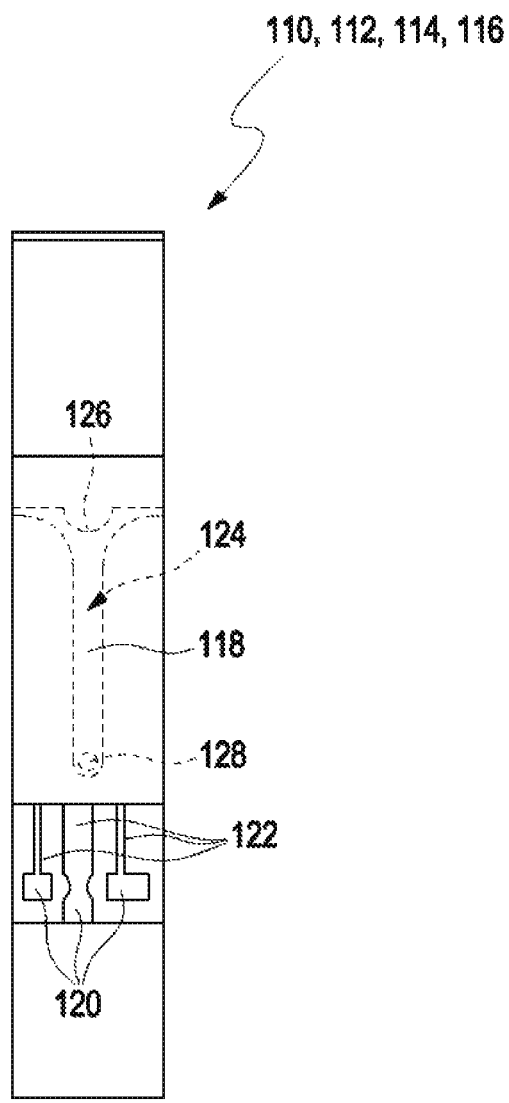
FIGS. 1A to 1B show an exemplary embodiment of a test element in a back view (FIG. 1A) and in a front view (FIG. 1B)
Figure 1:
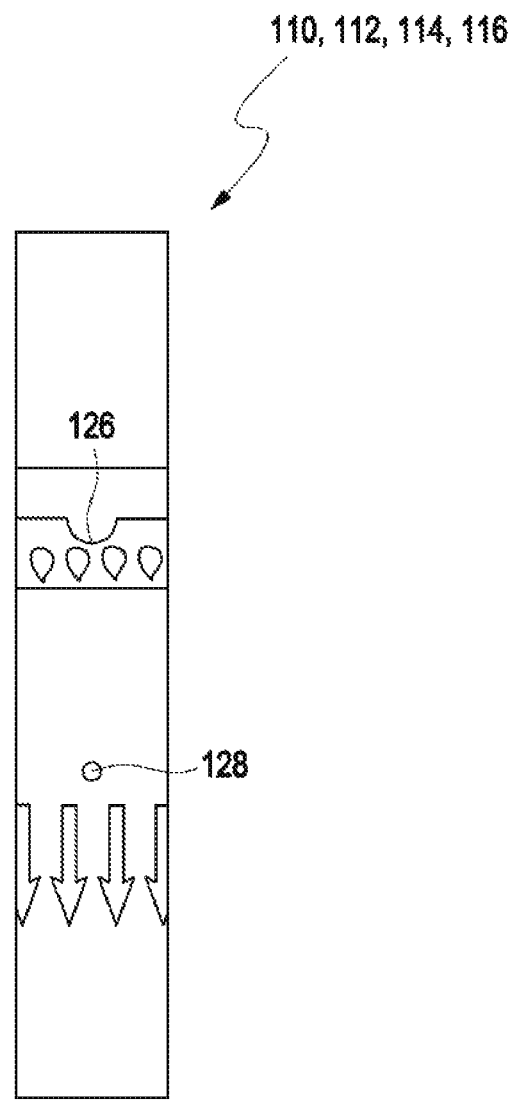

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The present disclosure is directed to a test element analysis system for the analytical examination of a sample and a method for determining whether a test element located inside a test element holder of a test element analysis system for the analytical examination of a sample has sufficient thermal contact with an electrical heating element configured for electrically heating the test element.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "typically", "more typically", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

In accordance with one embodiment of the disclosure, a test element analysis system for the analytical examination of a sample, in particular of a body fluid, is disclosed. The test element analysis system comprises at least one evaluation device. The evaluation device comprises at least one test element holder for positioning a test element containing the sample. Further, the evaluation device comprises at least one measuring device for measuring a change in a measuring zone of the test element, the change being characteristic for the analyte or the parameter to be determined. The test element analysis system further comprises at least one electrical heating element configured for electrically heating the test element and at least one electrical power supply for supplying electrical energy to the electrical heating element. Further, the test element analysis system comprises at least one temperature sensor connected to the test element holder for detecting a temperature of the test element holder and at least one gap detection device configured for monitoring the electrical energy $E_{spez}$ supplied by the electrical power supply to the electrical heating element for reaching a predetermined target temperature measured by the temperature sensor.

As further used herein, the term "system" refers to an arbitrary set of interacting component parts forming a whole. Specifically, the components may interact with each other in order to fulfill at least one common function. The components may be handled independently or may be coupled or connectable to each other. Thus, the term "test element analysis system" generally refers to a group of at least two elements or components which are capable of interacting in order to perform at least one analytical detection by interacting with an arbitrary test element, specifically at least one analytical detection of at least one analyte or parameter of the sample. The test element analysis system may generally also be referred to as an analytical system, an analytical kit, a sensor system or a measurement system.

As generally used within the present disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes or blood coagulation disorders. However, additionally or alternatively, the disclosure may be applied to other types of users or patients.

As further used herein the term "sample" may refer to an arbitrary material or combination of materials taken for an analysis, testing or investigation. The sample may be a limited quantity of something which is intended to be similar to and may represent a larger amount. However, the sample may also comprise a full specimen. The sample may be solid sample, a liquid sample or a gaseous sample or a combination of these. Specifically, the sample may be a fluid sample, i.e., a sample which is fully or partially in a liquid state and/or in a gaseous state. A quantity of the sample may be describable in terms of its volume, mass or size. However, other dimensions are feasible. The sample may comprise only one material or only one compound. Alternatively, the sample may comprise several materials or compounds.

The term "analyte" generally refers to an arbitrary element, component or compound which may be present in the sample and the presence and/or the concentration may be of interest for the user, the patient or medical staff such as a medical doctor. Particularly, the analyte may be or may comprise an arbitrary chemical substance or chemical compound which may take part in the metabolism of the user or the patient, such as at least one metabolite. The detection of the at least one analyte specifically may be an analyte-specific detection.

The term "parameter" generally may refer to an arbitrary value such as a measurement value which is obtainable within or by an analytical test. Exemplarily, the parameter may correspond to a property of the sample and/or a property of the at least one analyte as described above. Specifically, the parameter may be a coagulation parameter such as to a coagulation time of the analyte. For further details on the term "coagulation parameter" as further used herein, reference may be made to U.S. Appln. Pub. No. 2006/0035298 A1, the disclosure of which is hereby incorporated herein by reference.

As further used herein, the term "body fluid" may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue.

The term "analytical examination" generally may refer to a process of determining the presence and/or the quantity and/or the concentration of the at least one analyte or to a process of determining a parameter of the sample which is characteristic of the properties of the sample, e.g., a coagulation parameter which is characteristic of the coagulation properties of a blood sample. The detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one measurement signal specifically may be or may comprise at least one electronic signal such as at least one voltage and/or at least one current. The at least one signal may be or may comprise at least one analogue signal and/or may be or may comprise at least one digital signal.

The test element analysis system may further comprise at least one test element. The term "test element" generally may refer to an arbitrary device which is capable of detecting the analyte in the sample or of determining the parameter of the sample. The test element may specifically be a strip-shaped test element. As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10 and most typically by at least a factor of 20 or even at least a factor of 30. Thus, the test element may also be referred to as test strip.

The test element may comprise at least one component or at least one reagent which changes at least one detectable property when the analyte is present in the sample such as a test chemistry. The term "test chemistry", also referred to as "test chemical", may refer to an arbitrary material or a composition of materials adapted to change at least one detectable property in the presence of the analyte. Generally, this property may be selected from an electrochemically detectable property and/or an optically detectable property, such as a color change and/or a change in remissive properties. Specifically, the test chemistry may be a highly selective test chemistry, which only changes the property if the analyte is present in the sample of the body fluid applied to the test element, whereas no change occurs if the analyte is not present. More typically, the degree or change of the property may be dependent on the concentration of the analyte in the body fluid, in order to allow for a quantitative detection of the analyte.

Specifically, the test element may comprise at least one reagent configured for activating a coagulation of components of the body fluid. The reagent may comprise reactive components of thromboplastin and a peptide substrate. Thus, in case the reagent is exposed to the sample, the thromboplastin may activate a clotting and thrombin may be generated. Thrombin may cleave the peptide substrate and an electrochemical signal may be generated. The electrochemical signal may be evaluated with regard to a time of its occurrence. However, other reagents and/or measurement principles may be feasible.

As used herein, the term "electrochemical detection" refers to a direct or indirect, e.g., via a redox mediator, detection of an electro-chemically detectable property of the analyte, such as an electrochemical detection reaction. Thus, for example, the electrochemical detection reaction may be detected by comparing one or more electrode potentials, such as a potential of a working electrode with the potential of one or more further electrodes such as a counter electrode or a reference electrode. The detection may be analyte specific. The detection may be a qualitative and/or a quantitative detection.

The test element may have the at least one measuring zone capable of performing at least one change being characteristic for the analyte or the parameter. As further used herein, the term "measuring zone" may refer to an arbitrary area or region of an object wherein an arbitrary measurement, specifically an analytical measurement, is conducted. Specifically, the test chemistry as described above may be located within the measuring zone, particularly on a surface of the measuring zone.

The test element may be an electrochemical test element. The term "electrochemical test element" may refer to an arbitrary test element configured for conducting at least one electrochemically detection. As used herein, the term "electrochemically detection" refers to a detection of an electro-chemically detectable property of at least one arbitrary analyte, such as an electrochemical detection reaction. Thus, for example, the electrochemical detection reaction may be detected by comparing one or more electrode potentials, such as a potential of a working electrode with the potential of one or more further electrodes such as a counter electrode or a reference electrode. The detection may be analyte specific. The detection may be a qualitative and/or a quantitative detection.

The test element may comprise at least one capillary configured for receiving the sample. The term "capillary" generally refers to an arbitrary small, elongate void volume such as a small tube. Generally, the capillary may comprise dimensions in the millimeter or sub-millimeter range. Commonly, a fluidic medium may migrate through the capillary by capillary action wherein the fluidic medium may flow in narrow spaces of the capillary without an assistance of external forces like gravity due to intermolecular forces between the fluidic medium and a surface of the capillary facing the fluidic medium.

The term "evaluation device" may generally refer to an arbitrary device being configured to derive at least one item of information from data. Specifically, the evaluation device may be configured to derive the at least one item of information regarding the presence and/or concentration of the analyte in the body fluid or regarding a parameter of the body fluid from at least one signal.

As described above, the evaluation device comprises the measuring device. The term "measuring device" generally may refer to an arbitrary device, typically an electronic device, which may be configured to detect at least one signal. The signal may be an optical signal and/or an electrochemical signal. The measuring device may be handled independently from the test element and may be adapted to interact with the test element in order to perform an analysis, such as by detecting the at least one signal. Thus, the term "measuring device" may often also be referred to as a measurement device, an analytical device, a meter or a test device. The term "measurement value" may generally refer to an arbitrary value which is provided by a measuring device. Specifically, the measurement value may correspond to a value which corresponds to at least one detected signal or which is derived from the detected signal.

As described above, the evaluation device comprises the test element holder. The term "test element holder" generally may refer to an arbitrary object which is configured to receive or to hold an arbitrary test element. Specifically, the test element may be positioned on a specific position within the test element holder such that a movement of the test element in at least one direction may be suppressed at least to a large extend. Thus, the measurement zone of the test element may be located in a predetermined position relative to the measuring device. The test element may specifically be configured to be put reversibly into the test element holder. Thus, the test element may be removable from the test element holder without further ado. Still, other embodiments are feasible. The test element may be at least partially received in the test element holder. The term "being received" may generally refer to a condition of an object of being located or inserted fully or at least partially into a receptacle or into an opening of another element. Thus, a part of the object may be located outside of the other element. Exemplarily, the test element holder may comprise at least one receptacle configured for receiving the test element. Thus, the receptacle may be shaped complementary to the test element. Therefore, the receptacle and the test element may be configured to establish a form-fit connection. Still, other embodiments are feasible.

The term "electrical heating element" may refer to an arbitrary element which is configured to load thermal energy to another object. Thereby, the thermal energy may be produced by the electrical heating element such as by transforming one type of energy into another type of energy. Therefore, the electrical heating element may comprise at least one electrical heat source. The term "electrical heat source" may refer to an arbitrary device which is configured to convert electrical energy into thermal energy. Additionally or alternatively, the electrical heating element may be configured to transport energy to the other object. Exemplarily, the electrical heating element may comprise at least one thermal resistor.

The electrical heating element may comprise at least one flat supporting surface for the test element. As further used herein, the term "supporting surface" may refer to an arbitrary surface which is configured to hold an arbitrary element. The supporting surface may be configured to establish a close connection to the element. Therefore, the supporting surface may specifically be a flat and/or a smooth surface. The element may be configured to lie slackly on the supporting surface. However, the supporting surface may have a receptacle which may be shaped complementary to the element and/or may comprise a fixing element such as a spring element such that a movement of the element on the supporting surface may be suppressed at least to a large extend.

Exemplarily, the electrical heating element may comprise at least one ceramic plate. The ceramic plate may be in thermal contact with at least one electrical heat source, specifically with the thermal resistor. The term "thermal contact" may refer to a property of two or more elements of being arranged in such a manner that thermal energy may be transferable from one element to another one. As further used herein, the term "insufficient thermal contact" may refer to a property of an arbitrary contact between two or more elements of being arranged in such a manner that no or only less thermal energy may be transferable from one element to another element. This may exemplarily be the case when the two or more elements are arranged in distance to each other. On the contrary, the term "sufficient thermal contact" may refer to a property of two or more elements of being arranged in such a manner that thermal energy may be transferable from one element to another one in a desired amount and/or in an amount which is adequate for a certain purpose.

The ceramic plate may comprise at least one heating surface facing the test element being positioned in the test element holder. The test element may be in thermal contact with the heating surface. The term "heating surface" may refer to an arbitrary surface which is configured to transfer thermal energy to another object. The heating surface may optionally be identical to the flat supporting surface. Specifically, the temperature sensor may be in thermal contact with the ceramic plate on a reverse side of the ceramic plate. Thereby, the reverse side may oppose the heating surface. The electrical heating element may either be fully or partially be part of the test element holder, such as by being fully or partially integrated therein, or may fully or partially be embodied as a separate device. Consequently, the term "the temperature sensor being connected to the test element holder for detecting a temperature of the test element holder" may also imply the possibility of the temperature sensor monitoring the temperature of the at least one heating element and/or the temperature of at least one heating surface of the heating element, which fully or partially may be part of the test element holder. The temperature sensor specifically may be configured to monitor a temperature of the electrical heating element, specifically of the heating surface of the electrical heating element.

The term "side" may generally refer to an arbitrary component or part of an object which may be viewable from one perspective. In case the object has the shape of a cuboid, the term "side" may specifically refer to one surface of the cuboid. The term "reverse side" may be considered as description without specifying an order and without excluding a possibility that several kinds of reverse sides may be existent.

The term "electrical power supply" may refer to an arbitrary electrical device which is configured to provide electrical energy to another element, specifically to an electrical load. The electrical power supply may be configured to obtain energy from various types of energy sources, including electrical energy transmission systems, energy storage devices such as batteries or fuel cells, electromechanical systems such as generators, or other power supplies. The electrical power supply may be configured to convert one form of electrical energy to another one. Thus, the electrical power supply may also be referred to as electric power converter. Specifically, the electrical heating element may comprise at least one pulse-width modulated voltage source and/or at least one pulse-width modulated current source.

The term "sensor" may generally refer to an arbitrary device which is configured to detect a change of a physical, chemical and/or biological parameter or property of an environment or of an object. Therefore, the sensor may be a transducer as the sensor may be configured to convert the parameter or property into an arbitrary type of output. The term "temperature sensor" may refer to an arbitrary device which is configured to measure a temperature or a temperature gradient. The temperature sensor may therefore comprise some means for converting the measured temperature or the temperature gradient into a numerical value. Exemplarily, the temperature sensor may comprise at least one temperature dependent electrical resistor.

As further used herein, the term "gap detection device" may refer to an arbitrary device which is configured to determine whether an arbitrary object has sufficient thermal contact with another element, specifically with a heating element, or whether a gap exists which prevents or impedes a sufficient heat transfer between the object and the element. As used therein, the term "sufficient" may be defined by using a threshold method, which compares a thermal resistance with one or more thresholds and defines a thermal resistance to be "sufficient" in case the resistance is below the threshold or does not exceed the threshold. Instead of using a thermal resistance, a heat transfer rate under defined experimental conditions may be used, wherein a heat transfer rate having at least a threshold value or exceeding a threshold value is defined as "sufficient". The threshold value may be defined experimentally, such as by measuring thermal resistances and/or heat transfer rates in a normal state in which the system operates satisfactorily and without any failures.

As described above, the gap detection device is configured for monitoring the electrical energy $E_{spez}$ supplied by the electrical power supply to the electrical heating element for reaching a predetermined target temperature measured by the temperature sensor. The term "electrical energy $E_{spez}$" may generally refer to energy which is transferred via electricity or which is stored in electric fields. Specifically, the gap detection device may be configured for evaluating the electrical energy $E_{spez}$ supplied by the electrical power supply to the electrical heating element for reaching the predetermined target temperature and to derive at least one item of information on a thermal contact between the electrical heating element and the test element from the evaluation of the electrical energy $E_{spez}$. Specifically, the gap detection device may further be configured to compare the at least one item of information of the thermal contact between the electrical heating element and the test element with at least one threshold value in order to determine whether a sufficient thermal contact is given or not for performing an accurate measurement with the test element analysis system and the test element positioned in the test element holder. As used herein, the term "accurate" generally refers to a measurement leading to measurement results which are, at least within predetermined tolerances, identical to measurement results obtained by a calibration measurement such as a laboratory calibration measurement. Specifically, the gap detection device may be configured for one or more of the group of aborting the measurement, preventing the measurement, flagging the measurement and giving out a warning in case an insufficient thermal contact between the electrical heating element and the test element is detected.

Specifically, the gap detection device may be configured for determining whether one of the following situations is given: a situation in which a test element is located inside the test element holder, with the test element having a predetermined thermal contact with the electrical heating element; a situation in which no test element is located inside the test element holder or in which a test element is located inside the test element holder, the test element having an insufficient or no thermal contact with the electrical heating element. Therefore, the gap detection device may be configured for comparing the electrical energy $E_{spez}$ or at least one value derived thereof with at least one threshold value in order to determine whether a sufficient thermal contact between the electrical heating element and the test element exists.

The term "target temperature" may generally refer to a desired temperature which an arbitrary system should reach. The term "predetermined" may generally refer to a property of being determined, stated or fixed before a certain event occurs or is introduced. Thus, the value of the target temperature may be defined before determining whether a test element located inside a test element holder of a test element analysis system for the analytical examination of a sample has sufficient thermal contact with electrical heating element. The term "threshold value" may generally refer to a minimum value which is necessary such that a certain, desired action or event occurs.

The gap detection device may be configured for normalizing the electrical energy $E_{spez}$ and to compare a normalized value of the electrical energy $E_{spez}$ with at least one threshold value in order to determine whether a sufficient thermal contact between the electrical heating element and the test element exists. The term "normalizing" may generally refer to a mathematical procedure of transforming an original value in a manner such that a normalized value is generated which may be comparable to other normalized values. Specifically, the normalized value of the electrical energy is determined by:

$$E_{std} = \frac{f_{dev} \cdot E_{spez} - E_\infty}{E_0 - E_\infty}. \tag{1}$$

$E_{std}$ may denote the normalized value of the electrical energy $E_{spez}$. $E_\infty$ may denote an electrical energy required to be supplied by the electrical power supply to the electrical heating element for reaching the predetermined target temperature in case no test element is positioned in the test element holder. $E_0$ may denote an electrical energy required to be supplied by the electrical power supply to the electrical heating element for reaching the predetermined target temperature in case a test element is positioned in the test element holder with no gap in between the electrical heating element and the test element. Further, $f_{dev}$ may denote a device dependent calibration factor and/or instrument-specific factor. Specifically, $E_\infty$, $E_0$ and $f_{dev}$ may be predetermined calibration parameters and/or instrument-specific parameters stored in a data storage device of the gap detection device.

The term "calibration" may refer to an evaluation and/or to a documentation of a deviation of a measured variable provided by an arbitrary measurement device or control unit from a right value of the measured variable. Thus, the calibration measurement may be conducted, specifically under defined conditions, in order to determine a correlation between an input parameter and an output parameter, specifically the measured variable. The correlation may be expressible by the calibration factor. For subsequent measurements using the calibrated device, the measured value may be correctable through the calibration factor and a corrected value of the measured variable may be used for evaluation.

The gap detection device may comprise at least one energy detection device. The term "energy detection device" may generally refer to an arbitrary device, typically an electronic device, which is configured to detect at least one signal related to an energy, specifically to an electrical energy. Specifically, the gap detection device may be configured for monitoring the electrical energy $E_{spez}$ supplied by the electrical power supply to the electrical heating element for reaching a predetermined target temperature measured by the temperature sensor. Specifically, the energy detection device may comprise at least one of a voltmeter or an amperemeter. However, other embodiments are feasible. Further, the gap detection device may comprise at least one data processing device with software configured for evaluating the electrical energy $E_{spez}$. The term "data processing device" may generally refer to an arbitrary device which is configured for calculating or processing data.

Further, the test element analysis system may comprise at least one electrical contact element for electrically contacting the test element, specifically, the electrochemical test element. As used herein, the term "contact element" generally refers to an arbitrary element which is electrically conductive. Further, the contact element may comprise one or more surfaces, specifically flat surfaces, which may be configured to establish a close connection to other electrically conductive elements.

In accordance with another embodiment of the present disclosure, a method for determining whether a test element located inside a test element holder of a test element analysis system for the analytical examination of a sample has sufficient thermal contact with electrical heating element configured for electrically heating the test element is disclosed. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method comprises:
a) inserting the test element into the test element holder;
b) heating the test element to a predetermined target temperature by using the electrical heating element;
c) monitoring the electrical energy supplied by an electrical power supply to the electrical heating element for reaching the predetermined target temperature;
d) evaluating the electrical energy supplied by the electrical power supply to the electrical heating element for reaching the predetermined target temperature and deriving thereof at least one item of information on a thermal contact between the electrical heating element and the test element.

The method may specifically be conducted by utilizing the test element analysis system according to any embodiment as described above or as further described below.

Step d) may specifically comprise comparing the electrical energy $E_{spez}$ or at least one value derived thereof with at least one threshold and determining whether a sufficient thermal contact between the electrical heating element and the test element exists. Further, step d) may comprise normalizing the electrical energy $E_{spez}$ and comparing a normalized value of the electrical energy $E_{spez}$ with at least one threshold value in order to determine whether a sufficient thermal contact between the electrical heating element and the test element exists.

The normalized value of the electrical energy may be determined by the above-mentioned formula (1). The method may further comprise at least one calibration step for determining calibration parameters $E_\infty$, $E_0$ and $f_{dev}$ and storing the calibration parameters in at least one data storage device. Commonly, the calibration parameters may be determined during production of the test element analysis system and may be stored on the test element analysis system such that the workload or handling steps on the user's side may be reduced. Specifically, step d) may be performed by using at least one data processing device, specifically a data processing device with software configured for evaluating the electrical energy $E_{spez}$.

The proposed test element analysis system for the analytical examination of a sample as well as the proposed method for determining whether a test element located inside a test element holder of a test element analysis system for the analytical examination of a sample has sufficient thermal contact with electrical heating element configured for electrically heating the test element provide many advantages over known devices and methods.

Usually, a lot of test elements may have to be heated to a certain temperature value, specifically in order to receive correct measurement results. Deviations of the temperature from a target temperature may lead to deviating measurement values. Therefore, it may generally be important, to know a correct temperature of the test element. Generally, common test element analysis systems comprise an additional temperature sensor directed to the test element or within a construction volume which is located above the test element. Additionally or alternatively, conductive paths may be used. The conductive paths and/or the temperature sensor may have to be electrically connected. This may specifically require further sensor elements and/or further electronic components in addition to the electrical heating element. The further sensor elements may cause an effect on a measurement result, may require a construction volume, may lead to a more complex test element analysis system and may lead to increased costs. Beyond, more complex and thus more expensive test elements may be required.

The test element analysis system according to the present disclosure comprises the electrical heating element. In case the test element lies on the supporting surface of the electrical heating element, the test element may be thermally well coupled to the electrical heating element. The heat capacity of the entire system comprising of at least the electrical heating element and the test element lying on the supporting surface of the electrical heating element which shall be heated may therefore be larger than in case the test element does not lie on the supporting surface of the electrical heating element. For heating the electrical heating element to the predetermined target temperature a higher amount of energy may be necessary in case the test element does lie on the supporting surface than in case the test element does not lie on the supporting surface. In case the test element does not lie on the supporting surface the electrical heating element is heated but not the test element in a first approximation. Via a gap detection algorithm it may be evaluated how fast the predetermined target temperature is reached and/or how much energy may therefore be necessary. Therefore, a quality of how good the test element is supported by and thermally coupled to the electrical heating element may be evaluated.

Summarizing the findings of the present disclosure, the following embodiments are typical:

Embodiment 1

A test element analysis system for the analytical examination of a sample, in particular of a body fluid, comprising:
at least one evaluation device with at least one test element holder for positioning a test element containing the sample and at least one measuring device for measuring a change in a measuring zone of the test element, the change being characteristic for the analyte;
at least one electrical heating element configured for electrically heating the test element;
at least one electrical power supply for supplying electrical energy to the electrical heating element;
at least one temperature sensor connected to the test element holder for detecting a temperature of the test element holder;
at least one gap detection device configured for monitoring the electrical energy $E_{spez}$ supplied by the electrical power supply to the electrical heating element for reaching a predetermined target temperature measured by the temperature sensor.

Embodiment 2

The test element analysis system according to the preceding embodiment, wherein the gap detection device is configured for evaluating the electrical energy $E_{spez}$ supplied by the electrical power supply to the electrical heating element for reaching the predetermined target temperature and to derive at least one item of information on a thermal contact between the electrical heating element and the test element.

Embodiment 3

The test element analysis system according to the preceding embodiment, wherein the gap detection device is further configured to compare the at least one item of information on the thermal contact between the electrical heating element and the test element with at least one threshold value in order to determine whether a sufficient thermal contact is given or not for performing an accurate measurement with the test element analysis system and the test element positioned in the test element holder.

Embodiment 4

The test element analysis system according to the preceding embodiment, wherein the gap detection device is configured for one or more of the group of aborting the measurement, preventing the measurement, flagging the measurement and giving out a warning in case an insufficient thermal contact between the electrical heating element and the test element is detected.

Embodiment 5

The test element analysis system according to any one of the preceding embodiments, wherein the gap detection device is configured for determining whether one of the following situations is given: a situation in which a test element is located inside the test element holder, with the test element having a predetermined thermal contact with the electrical heating element; a situation in which no test element is located inside the test element holder or in which a test element is located inside the test element holder, the test element having an insufficient or no thermal contact with the electrical heating element.

Embodiment 6

The test element analysis system according to any one of the preceding embodiments, wherein the gap detection device is configured for comparing the electrical energy $E_{spez}$ or at least one value derived thereof with at least one threshold value in order to determine whether a sufficient thermal contact between the electrical heating element and the test element exists.

Embodiment 7

The test element analysis system according to any one of the preceding embodiments, wherein the gap detection device is configured for normalizing the electrical energy $E_{spez}$ and to compare a normalized value of the electrical energy $E_{spez}$ with at least one threshold value in order to determine whether a sufficient thermal contact between the electrical heating element and the test element exists.

Embodiment 8

The test element analysis system according to the preceding embodiment, wherein the normalized value $E_{std}$ of the electrical energy $E_{spez}$ is determined by:

$$E_{std} = \frac{f_{dev} \cdot E_{spez} - E_\infty}{E_0 - E_\infty},$$

with $E_{std}$ denoting the normalized value of the electrical energy $E_{spez}$, $E_\infty$ denoting an electrical energy required to be supplied by the electrical power supply to the electrical heating element for reaching the predetermined target temperature in case no test element is positioned in the test element holder, $E_0$ denoting an electrical energy required to be supplied by the electrical power supply to the electrical heating element for reaching the predetermined target temperature in case a test element is positioned in the test element holder with no gap in between the electrical heating element and the test element, and $f_{dev}$ denoting a device dependent calibration factor.

Embodiment 9

The test element analysis system according to the preceding embodiment, wherein $E_\infty$, $E_0$ and $f_{dev}$ are predetermined calibration parameters stored in a data storage device of the gap detection device.

Embodiment 10

The test element analysis system according to any one of the preceding embodiments, wherein the gap detection device comprises at least one data processing device with software configured for evaluating the electrical energy $E_{spez}$.

Embodiment 11

The test element analysis system according to any one of the preceding embodiments, wherein the electrical power supply for supplying energy to the electrical heating element comprises at least one pulse-width modulated electrical power supply, specifically at least one pulse-width modulated voltage source and/or at least one pulse-width modulated current source.

Embodiment 12

The test element analysis system according to any one of the preceding embodiments, wherein the at least one temperature sensor comprises at least one temperature dependent electrical resistor.

Embodiment 13

The test element analysis system according to any one of the preceding embodiments, wherein the gap detection device comprises at least one energy detection device configured for monitoring the electrical energy $E_{spez}$ supplied by the electrical power supply to the electrical heating element for reaching a predetermined target temperature measured by the temperature sensor, wherein the energy detection device comprises at least one of a voltmeter or an amperemeter.

Embodiment 14

The test element analysis system according to any one of the preceding embodiments, wherein the electrical heating element comprises at least one thermal resistor.

Embodiment 15

The test element analysis system according to any one of the preceding embodiments, wherein the electrical heating element comprises at least one flat supporting surface for the test element.

Embodiment 16

The test element analysis system according to any one of the preceding embodiments, wherein the electrical heating element comprises at least one ceramic plate, wherein the at least one ceramic plate is in thermal contact with at least one electrical heat source, specifically with at least one thermal resistor, wherein the ceramic plate comprises at least one heating surface facing the test element being positioned in the test element holder, wherein the test element is in thermal contact with the heating surface.

Embodiment 17

The test element analysis system according to the preceding embodiment, wherein the temperature sensor is in thermal contact with the ceramic plate on a reverse side of the ceramic plate, the reverse side opposing the heating surface.

Embodiment 18

The test element analysis system according to any one of the preceding embodiments, wherein the test element is an electrochemical test element.

Embodiment 19

The test element analysis system according to the preceding embodiment, wherein the test element analysis system further comprises at least one electrical contact for electrically contacting the electrochemical test element.

Embodiment 20

The test element analysis system according to any one of the preceding embodiments, wherein the test element analysis system further comprises at least one test element.

Embodiment 21

The test element analysis system according to the preceding embodiment, wherein the test element comprises at least one capillary configured for receiving the sample.

Embodiment 22

The test element analysis system according to any one of the two preceding embodiments, wherein the sample is a blood sample and wherein the test element comprises at least one reagent configured for activating coagulation of the blood sample.

Embodiment 23

The test element analysis system according to any one of the three preceding embodiments, wherein the test element holder comprises at least one receptacle configured for receiving the test element.

Embodiment 24

The test element analysis system according to any one of the preceding embodiments, wherein the electrical power supply and the gap detection device are provided as one unit.

Embodiment 25

The test element analysis system according to any one of the preceding embodiments, wherein the electrical heating element is fully or partially part of the test element holder.

Embodiment 26

The test element analysis system according to any one of the preceding embodiments, wherein the temperature sensor is configured to monitor a temperature of the electrical heating element, particularly of the heating surface of the electrical heating element.

Embodiment 27

A method for determining whether a test element located inside a test element holder of a test element analysis system for the analytical examination of a sample has sufficient thermal contact with an electrical heating element configured for electrically heating the test element, the method comprising:
  a) inserting the test element into the test element holder;
  b) heating the test element to a predetermined target temperature by using the electrical heating element;
  c) monitoring the electrical energy $E_{spez}$ supplied by an electrical power supply to the electrical heating element for reaching the predetermined target temperature;
  d) evaluating the electrical energy $E_{spez}$ supplied by the electrical power supply to the electrical heating element for reaching the predetermined target temperature and deriving thereof at least one item of information on a thermal contact between the electrical heating element and the test element.

Embodiment 28

The test element analysis system according to the preceding embodiment, wherein step d) comprises comparing the electrical energy $E_{spez}$ or at least one value derived thereof with at least one threshold value and determining whether a sufficient thermal contact between the electrical heating element and the test element exists.

Embodiment 29

The method according to any one of the preceding method embodiments, wherein step d) comprises normalizing the electrical energy $E_{spez}$ and comparing a normalized value $E_{std}$ of the electrical energy $E_{spez}$ with at least one threshold value in order to determine whether a sufficient thermal contact between the electrical heating element and the test element exists.

Embodiment 30

The method according to any one of the two preceding method embodiments, wherein the normalized value $E_{std}$ of the electrical energy $E_{spez}$ is determined by:

$$E_{std} = \frac{f_{dev} \cdot E_{spez} - E_\infty}{E_0 - E_\infty},$$

with
$E_{std}$ denoting the normalized value of the electrical energy $E_{spez}$,
$E_\infty$ denoting an electrical energy required to be supplied by the electrical power supply to the electrical heating element for reaching the predetermined target temperature in case no test element is positioned in the test element holder,
$E_0$ denoting an electrical energy required to be supplied by the electrical power supply to the electrical heating element for reaching the predetermined target temperature in case a test element is positioned in the test element holder with no gap In between the electrical heating element and the test element, and
$f_{dev}$ denoting a device dependent calibration factor.

Embodiment 31

The method according to the preceding embodiment, wherein the method further comprises at least one calibration step for determining calibration parameters $E_\infty$, $E_0$ and $f_{dev}$ and storing the calibration parameters in at least one data storage device.

Embodiment 32

The method according to any one of the preceding method embodiments, wherein step d) is performed by using at least one data processing device, specifically a data processing device with software configured for evaluating the electrical energy $E_{spez}$.

In order that the embodiments of the present disclosure may be more readily understood, reference is made to the following examples, which are intended to illustrate the disclosure, but not limit the scope thereof.

FIGS. 1A and 1B show an exemplary embodiment of a test element 110 in a back view (FIG. 1A) and in a front view (FIG. 1B). The test element 110 may specifically be a strip-shaped test element 112 and may also be referred to as test strip 114. The test element 110 may specifically be an electrochemical test element 116. The electrochemical test element 116 may be configured for performing at least one electrochemically detection. Therefore, the test element 110 may have at least one measuring zone 118 capable of performing at least one change being characteristic for an analyte or a parameter of a sample. An electrical quantity may be measured by means of electrodes (not shown) provided in the measuring zone 118. The test element 110 may comprise electrically conductive contact surfaces 120. An electrical signal may be passed onto the electrically conductive contact surfaces 120 via conductor paths 122. The test element 110 may comprise at least one capillary 124 configured for receiving the sample. The capillary 124 may be configured such that a fluidic medium such as the sample may migrate through the capillary 124 by capillary action. The capillary 124 may comprise at least one inlet 126 and at least one ventilation opening 128.

Figure 2:
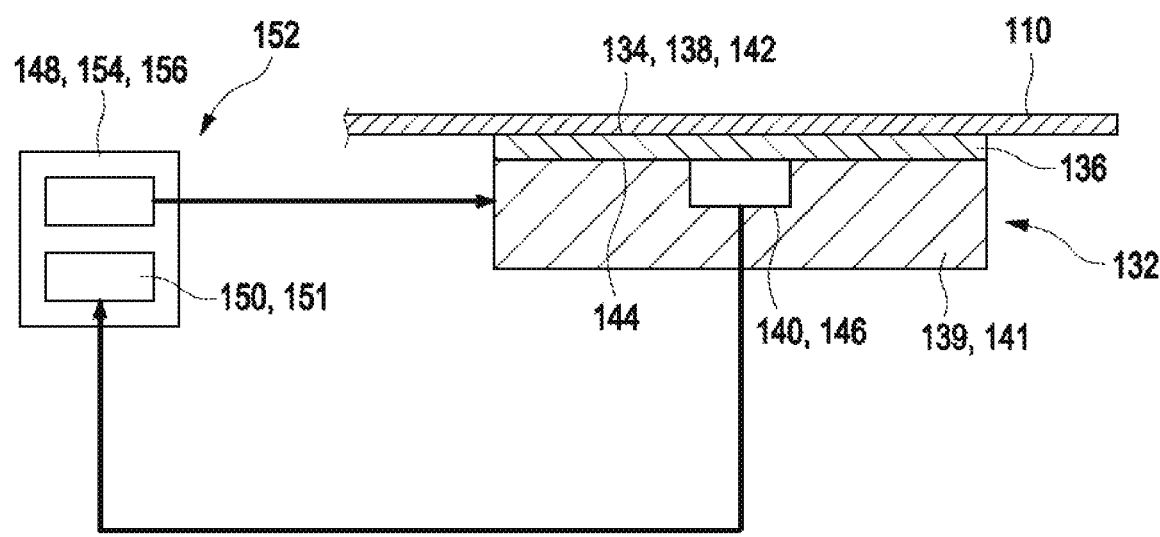
FIG. 2 shows components of a test element analysis system and a test element.

FIG. 2 shows components of a test element analysis system 130 and a test element 110. The test element 110 corresponds at least in wide parts to the test element 110 as illustrated in FIGS. 1A and 1B. Thus, reference may be made to the description of FIGS. 1A and 1B above.

Figure 3:
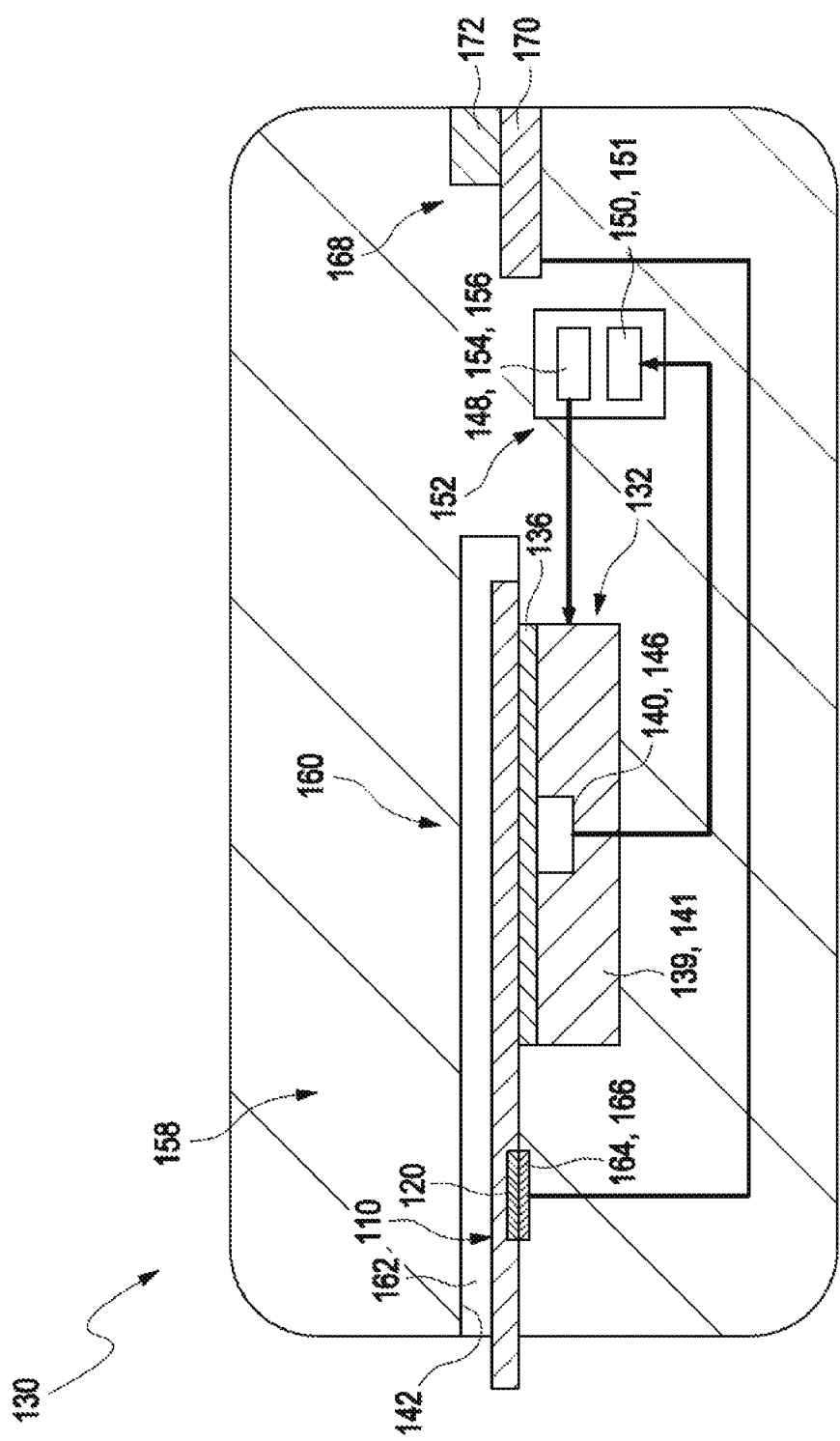
FIG. 3 shows an exemplary embodiment of a test element analysis system in a cross-sectional view.

The test element analysis system 130 comprises at least one electrical heating element 132 configured for electrically heating the test element 110. The electrical heating element 132 may comprise at least one flat supporting surface 134 for the test element 110. Exemplarily, the electrical heating element 132 may comprise at least one ceramic plate 136. The ceramic plate 136 may comprise at least one heating surface 138. The heating surface 138 may be identical to the flat supporting surface 134. The ceramic plate 136 may be in thermal contact with at least one electrical heat source 139, specifically with at least one thermal resistor 141. Further, the test element analysis system 130 comprises at least one temperature sensor 140 connected to a test element holder 142 as shown in FIG. 3 for detecting a temperature of the test element holder 142. The flat supporting surface 134 and/or the heating surface 138 may additionally be configured for holding the test element 110. The temperature sensor 140 may be in thermal contact with the ceramic plate 136 on a reverse side 144 of the ceramic plate 136, the reverse side 144 opposing the heating surface 138. The temperature sensor 140 may comprise at least one temperature dependent thermal resistor 146.

Further, the test element analysis system 130 comprises at least one electrical power supply 148 for supplying electrical energy $E_{spez}$ to the electrical heating element 132 and at least one gap detection device 150 configured for monitoring the electrical energy $E_{spez}$ supplied by the electrical power supply 148 to the electrical heating element 132 for reaching a predetermined target temperature measured by the temperature sensor 140. The gap detection device 150 may comprise at least one energy detection device 151. For further details about a functionality of the gap detection device 150 reference is made to the description above. The electrical power supply 148 and the gap detection device 150 may be provided as one unit 152. The electrical power supply 148 may comprise at least one pulse-width modulated electrical power supply 154 such as at least one pulse-width modulated voltage source 156.

FIG. 3 shows an exemplary embodiment of a test element analysis system 130 in a cross-sectional view. The test element analysis system 130 is configured for the analytical examination of a sample, in particular of a body fluid. The test element analysis system 130 comprises at least one evaluation device 158 with a test element holder 142 and a measuring device 160. Further, the test element analysis system 130 comprises at least one electrical heating element 132, at least one electrical power supply 148, at least one temperature sensor 140 and at least one gap detection device 150. The electrical heating element 132, the electrical power supply 148, the temperature sensor 140 and the gap detection device 150 correspond at least in wide parts to the electrical heating element 132, the electrical power supply 148, the temperature sensor 140 and the gap detection device 150 as illustrated in FIG. 2. Thus, reference may be made to the description of FIG. 2 above.

The test element holder 142 is configured for positioning a test element 110 containing the sample. Therefore, test element holder 142 may comprise at least one receptacle 162 configured for receiving the test element 110. Thus, the receptacle 162 may be shaped complementary to the test element 110. The receptacle 162 and the test element 110 may be configured to establish a form-fit connection. Specifically, the test element 110 may be positioned fixedly on a specific position within the test element holder 142 such that a movement of the test element 110 in at least one direction may be suppressed at least to a large extent. Thus, the measuring zone 118 of the test element 110 may be located in a predetermined position relative to the measuring device 160.

The measuring device 160 is configured for measuring a change in the measuring zone 118 of the test element 110, the change being characteristic for the analyte or the parameter of the sample. The test element holder 142 may comprise contact elements 164 with contact surfaces 166 which may allow an electrical contact between the electrically conductive contact surfaces 120 of the test element 110. The contact element 164 may be connected to measuring and evaluation electronics 168 which may be highly integrated in order to achieve a very compact construction and high degree of reliability. Measuring and evaluation electronics 168 may specifically comprise a printed circuit board 170 and an integrated circuit 172. Still, other embodiments are feasible.

Figure 4:
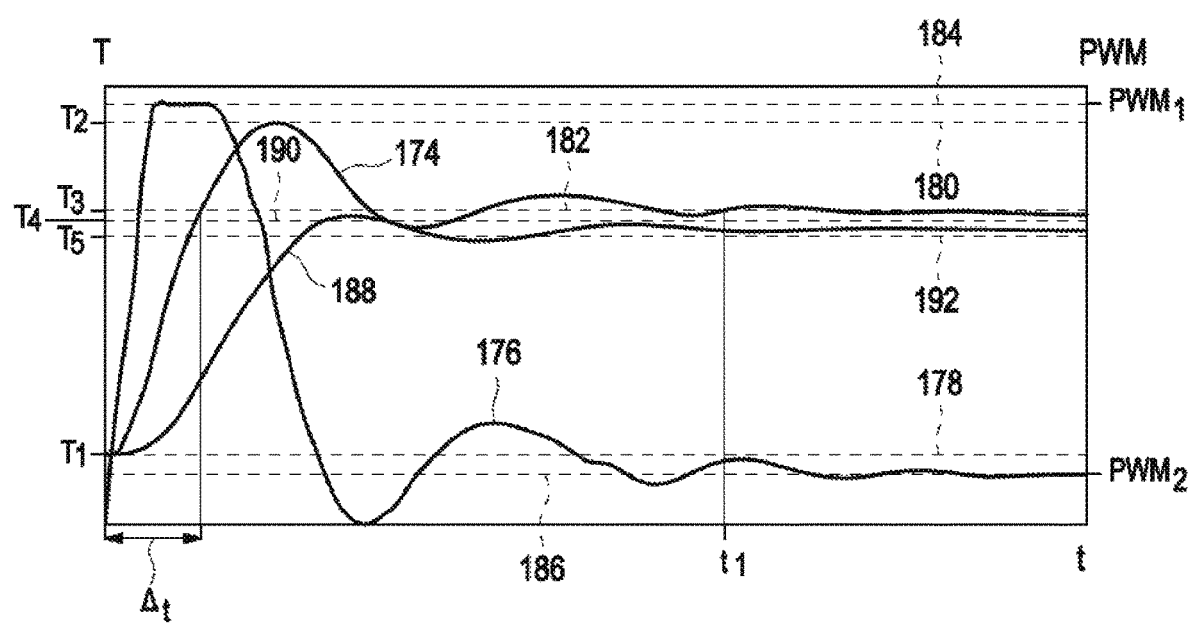
FIG. 4 shows an exemplary temperature profile of an electrical heating element and of a test element.

FIG. 4 shows an exemplary electrical heating element temperature profile 174 of an electrical heating element 132 and of a test element 110. The electrical heating element 132 and the test element 110 may correspond at least in large parts to the electrical heating element 132 as illustrated in FIG. 2 and the test element 110 may correspond at least on large parts to the test element 110 as depicted in FIGS. 1A and 1B. However, other embodiments are feasible.

An electrical heating element temperature profile 174 of the electrical heating element 132 is illustrated in FIG. 4. Thereby, a temperature T in dependence of a time t is shown. Additionally, a pulse-width modulation signal 176 of the electrical heating element 132 is illustrated. Thereby, a pulse-width modulation PWM in dependence of the time t is shown. The electrical heating element 132 may have a start temperature $T_1$ which is illustrated as a first line 178. When heating the electrical heating element 132, the electrical heating element temperature profile 174 may increase continuously and may reach a maximum temperature $T_2$ which is illustrated as a second line 180. Thereafter, the electrical heating element temperature profile 174 may settle out around a predetermined target temperature $T_3$ which is illustrated as a third line 182. The electrical energy $E_{spez}$ as described above may correspond to an energy input during a time interval $\Delta t$.

The pulse-width modulation signal 176 of the electrical heating element 132 may develop correspondingly. Thus, the pulse-width modulation signal 176 may increase continuously and may reach a maximum pulse-width modulation $PWM_1$ which is illustrated as a fourth line 184. Thereafter, the pulse-width modulation signal 176 may settle at a target pulse-width modulation $PWM_2$ which is illustrated as a fifth line 186.

Further, a test element temperature profile 188 of the test element 110 is illustrated in FIG. 4. When heating the electrical heating element 132, the test element temperature profile 188 may develop correspondingly to the electrical heating element temperature profile 188. The test element temperature profile 188 may increase continuously and may reach a maximum temperature $T_4$ which is illustrated as a sixth line 190 Thereafter, the test element temperature profile 188 may settle out around a predetermined target temperature $T_5$ which is illustrated as a seventh line 192. The predetermined target temperature $T_5$ of the test element 110 may be slightly less than the predetermined target temperature $T_3$ of the electrical heating element 132. Specifically, the predetermined target temperature $T_5$ of the test element 110 may be 37° C. However, slight deviations from this value or even a different value for the predetermined target temperature $T_5$ of the test element 110 may be feasible.

A measurement of a change in the measuring zone 118 of the test element 110 may be started at a time ti. The time ti may correspond to the time when the predetermined target temperature $T_5$ of the test element 110 is reached.

LIST OF REFERENCE NUMBERS 110 test element
112 strip-shaped test element
114 test strip
116 electrochemical test element
118 measuring zone
120 contact surface
122 conductor path
124 capillary
126 inlet
128 ventilation opening
130 test element analysis system
132 electrical heating element
134 flat supporting surface
136 ceramic plate
138 heating surface
139 heat source
140 temperature sensor
141 thermal resistor
142 test element holder
144 reverse side
146 temperature-dependent electrical resistor
148 electrical power supply
150 gap detection device
151 energy detection device
152 unit
154 pulse-width modulated electrical power supply
156 pulse-width modulated voltage source
158 evaluation device
160 measuring device
162 receptacle
164 contact element
166 contact surface
168 measuring and evaluation electronics
170 printed circuit board
172 integrated circuit
174 electrical heating temperature profile
176 pulse-width modulation signal
178 first line
180 second line
182 third line
184 fourth line
186 fifth line
188 test element temperature profile
190 sixth line
192 seventh line

What is claimed is:

1. A test element analysis system for the analytical examination of an analyte present in a sample, comprising:
    at least one evaluation device with at least one test element holder for positioning a test element containing the sample, and at least one measuring device for measuring a change in a measuring zone of the test element, the change being characteristic for an analyte present in the sample;
    at least one electrical heating element configured for electrically heating the test element;
    at least one electrical power supply for supplying electrical energy to the electrical heating element;
    at least one temperature sensor connected to the test element holder for detecting a temperature of the test element holder;
    at least one gap detection device configured for monitoring the electrical energy $E_{spez}$ supplied by the electrical power supply to the electrical heating element for reaching a predetermined target temperature measured by the temperature sensor, wherein the gap detection device is configured for evaluating the electrical energy $E_{spez}$ supplied by the electrical power supply to the electrical heating element for reaching the predetermined target temperature and to derive at least one item of information on a thermal contact between the electrical heating element and the test element based on the evaluation of the electrical energy $E_{spez}$.

2. The test element analysis system according to claim 1, wherein the sample is a body fluid.

3. The test element analysis system according to claim 1, wherein the gap detection device is configured for comparing the electrical energy $E_{spez}$ or at least one value derived thereof with at least one threshold value in order to determine whether a sufficient thermal contact between the electrical heating element and the test element exists.

4. The test element analysis system according to claim 1, wherein the gap detection device is configured for normalizing the electrical energy $E_{spez}$ and to compare a normalized value of the electrical energy $E_{spez}$ with at least one threshold value in order to determine whether a sufficient thermal contact between the electrical heating element and the test element exists.

5. The test element analysis system according to claim 1, wherein the gap detection device comprises at least one data processing device with software configured for evaluating the electrical energy $E_{spez}$.

6. The test element analysis system according to claim 1, wherein the gap detection device comprises at least one energy detection device configured for monitoring the electrical energy $E_{spez}$ supplied by the electrical power supply to the electrical heating element for reaching the predetermined target temperature measured by the temperature sensor, wherein the energy detection device comprises at least one of a voltmeter or an amperemeter.

7. The test element analysis system according to claim 1, wherein the electrical heating element comprises at least one flat supporting surface for the test element.

8. The test element analysis system according to claim 1, wherein the gap detection device is further configured to compare the at least one item of information on the thermal contact between the electrical heating element and the test element with at least one threshold value in order to determine whether a sufficient thermal contact is given or not for performing an accurate measurement with the test element analysis system and the test element positioned in the test element holder.

9. The test element analysis system according to claim 8, wherein the gap detection device is configured for one or more of the group of aborting the measurement, preventing the measurement, flagging the measurement and giving out a warning in case an insufficient thermal contact between the electrical heating element and the test element is detected.

10. The test element analysis system according to claim 1, wherein the test element analysis system further comprises at least one test element.

11. The test element analysis system according to claim 10, wherein the test element comprises at least one capillary configured for receiving the sample.

12. A method for determining whether a test element located inside a test element holder of a test element analysis system for the analytical examination of a sample has sufficient thermal contact with an electrical heating element configured for electrically heating the test element, the method comprising:
a) inserting the test element into the test element holder;
b) heating the test element by using the electrical heating element;
c) monitoring the electrical energy $E_{spez}$ supplied by an electrical power supply to the electrical heating element for reaching a predetermined target temperature of the electrical heating element; and
d) evaluating the electrical energy $E_{spez}$ supplied by the electrical power supply to the electrical heating element for reaching the predetermined target temperature of the electrical heating element and deriving thereof at least one item of information on a thermal contact between the electrical heating element and the test element.

13. The method according to claim 12, wherein step d) comprises comparing the electrical energy $E_{spez}$ or at least one value derived thereof with at least one threshold value and determining whether a sufficient thermal contact between the electrical heating element and the test element exists.

14. The method according to claim 12, wherein step d) comprises normalizing the electrical energy $E_{spez}$ and comparing a normalized value $E_{std}$ of the electrical energy $E_{spez}$ with at least one threshold value in order to determine whether a sufficient thermal contact between the electrical heating element and the test element exists.

15. The method according to claim 12, wherein step d) is performed by using at least one data processing device.

16. The method according to claim 15, wherein the data processing device includes software configured for evaluating the electrical energy $E_{spez}$.

* * * * *